United States Patent [19]

Weinberg et al.

[11] Patent Number: 5,395,763
[45] Date of Patent: Mar. 7, 1995

[54] CHROMOSOMAL EXPRESSION VECTOR

[75] Inventors: Robin A. Weinberg; Pamela A. De Ciechi, both of St. Louis; Mark G. Obukowicz, Kirkwood, all of Mo.

[73] Assignee: Monsanto Company, St. Louis, Mo.

[21] Appl. No.: 906,393

[22] Filed: Jun. 24, 1992

[51] Int. Cl.$^6$ .................. C12N 1/21; C12N 15/70; C12N 15/74
[52] U.S. Cl. .................. 435/252.3; 435/320.1
[58] Field of Search .................. 435/320.1, 69.1, 69.4, 435/172.1, 172.3, 252.3, 252.33, 252.34; 935/59, 66, 72, 23

[56] References Cited

U.S. PATENT DOCUMENTS

| | | | |
|---|---|---|---|
| 4,704,362 | 11/1987 | Itakura et al. | 435/252.3 |
| 4,716,105 | 12/1987 | Mizuuchi et al. | 435/5 |
| 4,830,965 | 5/1989 | Narang et al. | 435/172.3 |
| 4,845,031 | 7/1989 | Shub et al. | 435/69.1 |

FOREIGN PATENT DOCUMENTS

| | | |
|---|---|---|
| 8802078 | 8/1989 | Australia . |
| 0284126A | 9/1988 | European Pat. Off. . |
| WO85/01296 | 3/1985 | WIPO . |
| 8803169 | 5/1988 | WIPO . |

OTHER PUBLICATIONS

Castilho, B. A., P. Olfson and M. J. Casadaban. 1984. Plasmid insertion mutagenesis and lac gene fusion with mini-Mu bacteriophage transposons. J. Bacteriol. 158:488–495.

Mathee, K. and M. M. Howe. 1990. Identification of a positive regulator of the MU middle operon. J. Bacteriol. 172:6641–6650.

Higgins, N. P., P. Manlapaz-Ramos, R. T. Gandhi, and B. M. Olivera. 1983. Bacteriophage MU: A transposing replicon. Cell 33:623–628.

Hugo C. Gramajo, et al., Expression of cloned genes by in vivo insertion of tac promoter using a mini-Mu bacteriophage. (1988) Gene.65 305–314.

Norman Bauman, et al., Genentech Scores Basic U.S. Plasmid Patent. 1987. Bio/Technology vol. 5:1263.

N. Padukone, et al., λVectors for Stable Cloned Gene Expression. Biotechnol. Prog. 1990, 6, 277–282.

Nakano, E., et al., Construction of "Sleeper" Cloning Vehicles for Enzyme Overproduction. Agric. Biol. Chem. 46(1), 313–315 (1982).

Patterson et al. Gene vol. 50 (1986) pp. 101–109.

Olins et al. (1990) Methods in Enzymology pp. 115–119.

Primary Examiner—Richard A. Schwartz
Assistant Examiner—Kathleen L. Choi
Attorney, Agent, or Firm—Dennis A. Bennett

[57] ABSTRACT

A novel chromosomal expression vector based on the bacteriophage Mu is disclosed.

4 Claims, 10 Drawing Sheets

MudMon vector

1 Kan^r
transform to
Amp^r and Kan^r
→
2

Amp^r

Mu lysogen (ts)

amp
kan

3 Shift to 42°
Induce lysis by Mu

My lysate wt Mu

MudMon infect wild type

Select Kan^r Amp^S

5

1. Grow in LB 30°
to midlog
2. Shift to 42°
→
6

7

—— Mu DNA

CHROMOSOMAL EXPRESSION VECTOR

BACKGROUND OF THE INVENTION

1. Field of the Invention

This invention relates to gene expression and more particularly to a chromosomal expression vector based on the bacteriophage Mu.

2. Related Art

Over-expression of heterologous genes in E. coli has become a routine method as a first step for obtaining large amounts of pure protein. The heterologous gene is usually cloned downstream of a strong E. coli promoter on a multicopy plasmid. The amount of heterologous protein produced from such a system can account for as much as 40% of total cell protein. Although this system has been extremely useful, it does have some drawbacks. The major one is the instability of the multicopy plasmid. There is no system in place to ensure inheritance of most high copy number plasmids used in recombinant expression systems. If the copy number is high enough, mathematical models suggest that plasmid loss should not be a problem (Summers, 1991). However, high copy number recombinant plasmids are often not as stable as these models would predict (Summers, 1991). Any plasmidless cells that do appear often out grow those containing plasmids eventually leading to the loss of plasmid from nearly the entire population (Zund and Lebek, 1980).

The problem of plasmid instability is compounded when large volumes of cells are to be grown for production. This problem occurs during the large number of doublings in a chemostat for continuous culture or during subculturings to obtain an inoculum of appropriate size for a batch process. One common way to maintain the plasmid is to exert selective pressure, usually by the presence of an antibiotic. The inclusion of an antibiotic in the culture medium for large scale protein production can be a problem in terms of high cost and disposal. Furthermore, antibiotics such as β-lactams that are broken down can not always be used successfully to maintain the plasmid.

Several genetic methods have been described to overcome the problem of plasmid instability. Partition sequences from lower copy number plasmids have been included such as par (Skogman, et al. 1983), cer (Summers and Sherrat, 1984), and hok/sok (Gerdes, 1988). Although these systems do help stabilize the plasmid there is still plasmid loss when cells are grown in continuous culture. Another option is to include an essential gene on the plasmid such as ssb (Porter, et al., 1990). Any cells that lose the plasmid will die and not be able to overtake the population. This system has the disadvantage that the expression vector must replace a resident plasmid containing the essential gene.

A second factor leading to plasmid instability can be synthesis of a heterologous protein that is deleterious to the cell. In this case, any cells not making the protein will out compete those making the protein resulting in a plasmidless population. One way to circumvent this problem is to have expression of the gene very tightly regulated using promoters such as $P_{lac}$. However, it should be noted that it is unlikely that any promoter is ever entirely shut off and whatever low level transcription occurs will be multiplied by the high copy number.

The problems of instability and product lethality may be circumvented by having the heterologous gene present as a single copy on the chromosome prior to induction and present at many copies post-induction. Systems that use this switch in nature are lysogenic bacteriophage such as lambda. During the lysogenic state the phage is integrated as a single copy and is segregated with the chromosome at cell division ensuring inheritance. Upon induction of the lytic cycle the lambda genome is excised from the chromosome and replicates extrachromosomally resulting in as many as 100 copies. Lambda variants have been used to overexpress a limited number of genes (Padukone, et al., 1990, Nakano and Masuda, 1982 and Panasenko, et al., 1977). This system is not more widely used because the large genome size of lambda makes it cumbersome to work with and in some cases the cells lyse following induction.

The present invention is based on a different lysogenic bacteriophage, Mu. Mu differs from lambda in that it never replicates extrachromosomally. Upon induction of the lytic cycle Mu undergoes multiple rounds of replicative transposition resulting in as many as 100 copies of Mu DNA integrated into the host chromosome. All the replicative transposition functions including regulation of the switch from lysogenic to lytic phase are contained within a 4.5 kbp fragment on the left end of Mu thus eliminating the size problem encountered with lambda. Variants of Mu have been constructed that are capable of replicative transposition but are deleted for middle and late functions and therefore can not make phage particles. One such derivative, Mud4041, includes the Km-resistance antibiotic marker, allowing for easy selection of lysogens (Castilho, et al., 1984). To create a chromosomal expression vector, the Mu middle promoter, Pm, was introduced to regulate expression of heterologous genes. This promoter was chosen since it is induced following the start of Mu replication (Marrs and Howe, 1990, Stoddard and Howe, 1989). Induction of the promoter also requires the transactivator mor (Mathee and Howe, 1990). The Mu repressor of the lytic cycle, cts62, present on Mud4041 is temperature sensitive, therefore, by shifting the culture from 30° to 42° C., both replication of Mu and transcription from Pm will be induced. Using this system a number of heterologous proteins were made at 5 to 20% of total cell protein.

SUMMARY OF THE INVENTION

According to the present invention there is provided a new Mini Mu Vector, Consisting of:

1. Mu elements required for replicative transposition which include A, B, the two attachment sites attL and attR, and the genes encoding the regulatory proteins cts62 and ner; and a Mu mor gene, a Mu middle promoter, a ribosome binding site linked to at least one unique restriction site, and a gene encoding a selectable marker, all of which is operably linked to a DNA insert comprising codons for a preselected functional heterologous polypeptide or polypeptide intermediate therefor characterized in that the DNA insert is operably linked to and in proper reading frame relative to said Mu elements.

It is an object of the present invention to provide a new expression vector that is chromosomal based.

It is an advantage of the present invention in that a chromosomal based expression system as compared to a plasmid based system is the increased stability of the vector even in the absence of selective pressure. This feature should make this system extremely useful for production of recombinant proteins involving continuous culture or large scale batch fermentations.

It is another advantage of the present invention in that the size of the Mu is smaller and is therefore easier to manipulate than other chromosomal based systems.

It is still another advantage in that the present invention allows for tight regulation of expression of the heterologous gene. Any leakiness of the promoter would occur from one copy as opposed to the many that would be present in the standard plasmid vector systems.

Many other objects and purposes of the invention will be clear from the following descriptions of the invention.

While the specification concludes with claims particularly pointing out and specifically claiming the subject matter regarded as forming the present invention, it is believed that the invention will be better understood from the following detailed description of preferred embodiments taken in conjunction with the accompanying drawings.

DETAILED DESCRIPTION OF THE DRAWINGS

FIG. 1. Schematic outline for the construction of Mu expression vector. Using PCR, the Mor-Pm fragment (Mu bp 8751-9238 (Priess, et al., 1987)) was cloned into the BamHI site of pBC4041 as a BglII-BamHI fragment. The primers used were 5' ATGCCAGAAAGATCT-GGAGGATG 3' [SEQ ID NO:1] and 5' TTCCCCGGATCCGTTATTCA 3' [SEQ ID NO:2] AND included restriction sites for BglII and BamhI. The resulting mini-Mu has been named MudMON100. The g10L translation enhancer region from phage T7 (Olins and Rangwala, 1990) and a multiple cloning site were cloned from pMON5766 using PCR. The primers used were 5' GGCGCGTGGATCCGCTATCG 3' [SEQ ID NO:3] AND 5' ACAGAACA-GATCTGGGCCCTTC 3' [SEQ ID NO:4] making BglII and BamHI sites available for cloning. This fragment was inserted into the BamHI site of MudMON100. The resulting construct was named MudMON200. Restriction sites within parentheses were introduced by PCR. The bold line indicates mini-Mu DNA. All fragments derived by PCR were sequence confirmed using the Genesis 2000 system from DuPont. Insertion of heterologous genes is described in Table 1.

FIG. 2. Schematic outline of the protocol for isolation of desired mini-Mu lysogen and its induction. The gene of interest is cloned into the mini-Mu plasmid vector. This plasmid is used to transform a temperature sensitive Mu lysogen. This lysogen is then induced to produce a lysate which is used to transduce a non-Mu lysogen selecting for kanamycin-resistance. These resistant colonies are mini-Mu lysogens. To induce replication and transcription from the Mu middle promoter, the lysogen is grown at 30° C. to midlog phase and then shifted to 42° C.

FIG. 3. Southern blot analysis of stability of MudMON101 in MH4997. MH4997 (MudMON101) was subcultured for 7 d in LB in the absence of Km. The culture was diluted and spread on LB agar plates ∓ Km for single colonies. Six colonies were picked from each plate and grown overnight to obtain chromosomal DNA. The DNA was isolated as described in Materials and Methods. DNA (7 ug) was digested with HindIII and separated on a 0.8% agarose gel. The DNA was blotted onto Magnagraph nylon (MSI). The blot was probed with pBC4041 that was labelled with digoxigenin-dUTP and developed as described in Materials and Methods. Lane a. Km control. DNA was isolated from a fresh LB+Km overnight culture of MH4997(MudMON101) started from a freezer stock. Lanes b-g. DNA from overnight culture of colony that appeared on LB-Km plate following 7 d of subculturing. Lane h. No Km control. As in Lane a. DNA was isolated from a fresh overnight culture started from a freezer stock except no Km was added to the medium. Lanes i-n. DNA from overnight culture of colony that appeared on LB plate following 7 d of subculturing. The diagram below indicates the HindIII sites in MudMON101; I=internal fragment, F=flanking region.

FIG. 4a, 4b, and 4c. Induction of CAT expression in MH4997(MudMON101). Cells were grown in LB at 30° C. until they reached a Klett value of 80-100 (green filter). To induce Mu replication, an equal volume of LB prewarmed to 55° C. was added to the culture and the flasks were immediately placed at 42° C. Samples were taken at preinduction and at various time points post-induction.

A. MH4997(MudMON101) samples were assayed for CAT as described by Shaw (1975). Specific activity was defined as mmoles of Cm acetylated/min/mg protein. Protein concentration was determined by the BCA assay according to the manufacturer's instructions (Pierce). Two lysogens were assayed. Expression of CAT from JM101[pACYC184] was included as a positive control ■. The two stippled bars are two lysogens. B. SDS-PAGE analysis of CAT production. One ml samples taken at time points indicated were pelleted for 10 min. in a microfuge. JM101[pACYC184] was run as a control. The cells were sonicated in 50 mM Tris-HCl, pH7.8, 30 mM DTT. Samples (100 mg) were loaded on a 12.5% Laemmli (1970) SDS-PAGE.

C. Replication of MudMON101 in MH4997. A lysogen was induced as described in FIG. 2. Chromosomal DNA was isolated from cells taken at 0 (pre-induction), 1,2,3, and 4 h post-induction. DNA at concentrations indicated were spotted onto nitrocellulose following denaturation. The filter was baked in vacuo at 80° C. for 2 h. The blot was probed with $^{32}$P-labelled CAT gene from pCM4 that had been made using the Multiprime kit (Boehringer-Mannheim).

FIG. 7. Induction of MH4997(MudMON102) in LB. The level of expression of lacZ was monitored by assaying for β-galactosidase in cell extracts at various time points post-induction. Controls are MH4997 ■ and MH4997 (Mud4041) ■. The two stippled bars are 2 lysogens.

A. MH4997(MudMON201) was induced in LB and accumulation of pST was monitored by SDS-PAGE.

The level of induction was compared to that obtained with the plasmid vector pMON5723.

B. MudMON201 lysogens in MH4997(a), W3110G (b) and JM101(c) were induced in LB and the level of pST production compared 4 h post-induction by SDS-PAGE.

A. MH4997(MudMON202) was induced in LB and the level of hGH accumulated was determined by SDS-PAGE. For comparison, an induction was done from the plasmid pMON6369.

B. MudMON202 lysogens in MH4997(a), W3110G (b), JM101(c), and MH2374(d) were induced and the level of hGH present 4 h post-induction was determined by SDS-PAGE.

DETAILED DESCRIPTION OF THE PREFERRED EMBODIMENTS

Abbreviations

A = absorbance
Ap$^r$ = ampicillin-resistance
attR = right attachment site of Mu
bp = base pair(s)
βGal = β-galactosidase
CAA = casamino acids
CAT = Cm acetyltransferase
Cm$^r$ = chloramphenicol-resistance
E. = Escherichia
hGH = human growth hormone
IPTG = isopropyl-β-D-thiogalactopyranoside
Km$^r$ = Kanamycin-resistant
kbp = kilobase pair(s)
lac = lactose utilizing operon
LB = Luria broth
MCS = multiple cloning site
mor = middle operon regulator from Mu(E17)
nptII = neomycin phosphotransferase gene
PAGE = polyacrylamide gel electrophoresis
PCR = polymerase chain reaction
Pm = Mu middle promoter
pST = porcine somatotropin
rrnB = rRNA operon
SB = super broth
SDS = sodium dodecyl sulfate
Tn = transposon The present invention is based on a lysogenic bacteriophage, Mu. Mu differs from lambda in that it never replicates extrachromosomally. Upon induction of the lytic cycle Mu undergoes multiple rounds of replicative transposition resulting in as many as 100 copies of Mu DNA integrated into the host chromosome. All the replicative transposition functions including regulation of the switch from lysogenic to lytic phase are contained within a 4.5 kbp fragment on the left end of Mu, thus eliminating the size problem encountered with lambda. Variants of Mu have been constructed that are capable of replicative transposition but are deleted for middle and late functions and therefore can not make phage particles. One such derivative, Mud4041, includes the Km-resistance antibiotic marker, allowing for easy selection of lysogens (Castilho, et al., 1984). To create a chromosomal expression vector, the Mu middle promoter, Pm, was introduced to regulate expression of heterologous genes. This promoter was chosen since it is induced following the start of Mu replication (Marrs and Howe, 1990, Stoddard and Howe, 1989). Induction of the promoter also requires the transactivator Mor (Mathee and Howe, 1990). The Mu repressor of the lytic cycle, cts62, present on Mud4041 is temperature sensitive, therefore, by shifting the culture from 30° to 42° C., both replication of Mu and transcription from Pm will be induced. Using this system a number of heterologous proteins were made at 5 to 20% of total cell protein.

The mini-Mu vector described is based on bacteriophage Mu, a phage that has the properties of a transposon. Mu replicates by a method termed replicative transposition rather than as a plasmid. Upon infection of the cell with Mu, one copy of the Mu genome integrates randomly into the host chromosome. The proteins encoded by genes A and B catalyze the replication of the Mu DNA on the chromosome and insertion of a second copy elsewhere in the chromosome. During the course of a lytic infection, the process of replicative transposition is repeated many times resulting in as many as 100 copies of Mu DNA within the host chromosome. As a result of these multiple insertions, a great number of host genes may be mutated. However, in each cell the genes mutated may be different. The DNA of the host chromosome is rearranged resulting in inversions.

The mini Mu vector described consists of all the parts of bacteriophage Mu that are necessary for replicative transposition, A, B, the two attachment sites attL and attR as well as the genes encoding the regulatory proteins cts62 and ner. These gene products allow the vector to undergo replicative transposition and this process can be regulated by temperature shift. Some genes of Mu that are not essential for Mu replication but that increase its efficiency are not present on this vector. Therefore, the final copy number achieved is not as high as that seen with wild type Mu. The vector also contains the mor gene which encodes a positive regulator of transcription of the Mu middle promoter. The Mu middle promoter is included as well. Heterologous gene expression is under the control of the Mu middle promoter. Also included in the vector is a gene encoding a selectable marker, preferably the left half of Tn5 including the nptII gene allowing for selection on kanamycin. Production of Mor is dependent on read through transcription from the nptII gene. Also included in this vector is a ribosome binding site preferably from phage T7 gene 10L which has been shown to increase translational efficiency. This sequence is positioned downstream of the Mu middle promoter, Pm, to enhance production of the heterologous protein. Just downstream of the ribosome binding site is a unique restriction site that can be used to insert the desired heterologous gene preferably between 2–4 and more preferably 3.

In order to get expression from the Mu middle promoter, two things are required, the mor gene product and Mu DNA replication. Thus, upon temperature shift of a strain containing the MudMON vector on its chromosome, many copies of the MudMON DNA are made including the heterologous gene of interest and high level transcription of the heterologous gene occurs from each copy.

Materials and Methods

1. Bacterial strains, plasmids and media. A list of strains and plasmids used in this work is given in Table 1.

Media used include L broth (Ausebel, et al., 1989), LB plates, superbroth (SB) (Ausebel, et al., 1989) and M9 supplemented with 0.4% glucose, 2 μg of thiamine/ml, 1 mM MgSO$_4$, 0.1 mM CaCl$_2$, 1.0% casamino acids (CAA) and trace minerals (Obukowicz, et al., 1988). Thymidine at 10 μg/ml was added as needed. 2X M9 media were made by doubling the concentration of M9 salts and CAA. Media components were purchased from Difco or Sigma. Antibiotics were added at 100 mg Ap/L, 25 mg Km/L and 20 mg chloramphenicol/L. Antibiotics were purchased from Sigma.

2. Transductions

All mini-Mu lysates were prepared in MC1040. Cells were grown in LB at 30° C. to a Klett value of 80–100 (green filter). An equal volume of LB preheated to 55° C. was added to the culture and the flask was placed at 42° C. for 20 min. The culture was then switched to 37° C. and incubated for 45 to 60 min. with vigorous aeration. Chloroform (1%), MgSO$_4$ (2 mM) and CaCl$_2$ (0.2 mM) were added and the culture was mixed vigorously. Cells were pelleted at 8,000 rpm in a Beckman J2-21 centrifuge for 10 min. The supernatant fraction was centrifuged a second time to remove remaining cells and debris. For transductions, an equal volume of an overnight culture of cells was mixed with freshly prepared lysate. The mix was incubated for 30 min. at 30° C., diluted 10 fold in LB, incubated for 1 h at 30° C. with aeration and then plated on the appropriate medium.

3. Copy number determinations.

The copy number of MudMON vectors following induction was determined by dot blot hybridization. Chromosomal DNA was isolated as described by Ausebel et al. (1989) using hexadecyl trimethylammonium bromide. DNA was spotted on to Magnagraph nylon (MSI) at equal concentrations as determined spectrophotometrically at A$_{260}$. Two-fold dilutions were done to help quantify the copy number. A sample taken before induction was used to determine the signal of a single copy. Southern blot analysis was done to determine that the original lysogen was single copy. To normalize the DNA loading, the blot was first probed with a 200 bp fragment of the rrnB gene labelled with digoxigenin-dUTP using the Genius kit (Boehringer-Mannheim) and was developed with Lumi-Phos (Boehringer-Mannheim). The blot was then stripped of the rrnB probe according to the manufacturer's instructions and reprobed with labelled nptII gene. The copy number in each 4 h sample was determined by comparing the intensity of the signal at various dilutions with the intensity of the signal of the pre-induction sample.

Results a. Vector Construction

Figure 1:
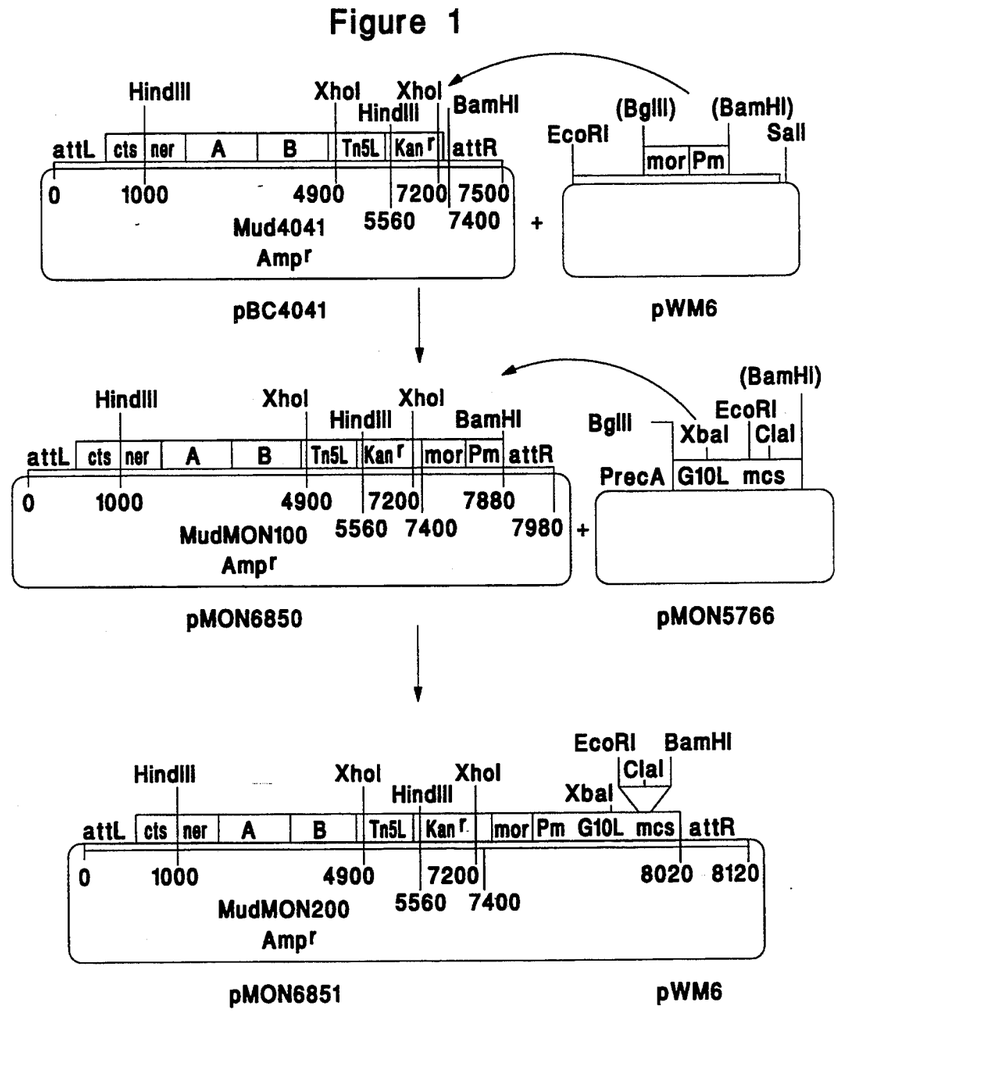

A chromosomal based expression vector was constructed based on the mini-Mu Mud4041(Castilho, et al., 1984). The Mud4041 was obtained from the laboratory of Malcolm Casadaban on pUC as pBC4041 (FIG. 1). This mini-Mu is capable of replicative transposition as it contains cts62, ner, A and B as well as left and right attachment sites attL and attR. It also contains the left end of Tn5 through nptII. The middle promoter of Mu, Pm, was chosen to control heterologous gene expression since it is induced following Mu replication. In this way both increased copy number and gene expression could be induced by temperature shift. Induction of Pm also requires a transactivator, the mor gene product (Mathee and Howe, 1990). Using PCR the mor gene and Pm were isolated from pWM6 (Margolin and Howe, 1986) and cloned into the unique BamHI site in pBC4041 as a BglII-BamHI fragment (8760–9231 bp of Mu (Priess, et al., 1987)) resulting in MudMON100 (FIG. 1). The mor gene is normally transcribed from the early promoter, Pe (Margolin, et al., 1989, Stoddard and Howe, 1989). However, expression of mor in this vector should be dependent on read through from the promoter for nptII. There is a transcriptional terminator at the end of mor (Stoddard and Howe, 1990) which should prevent read through expression of the heterologous gene.

Figure 2:
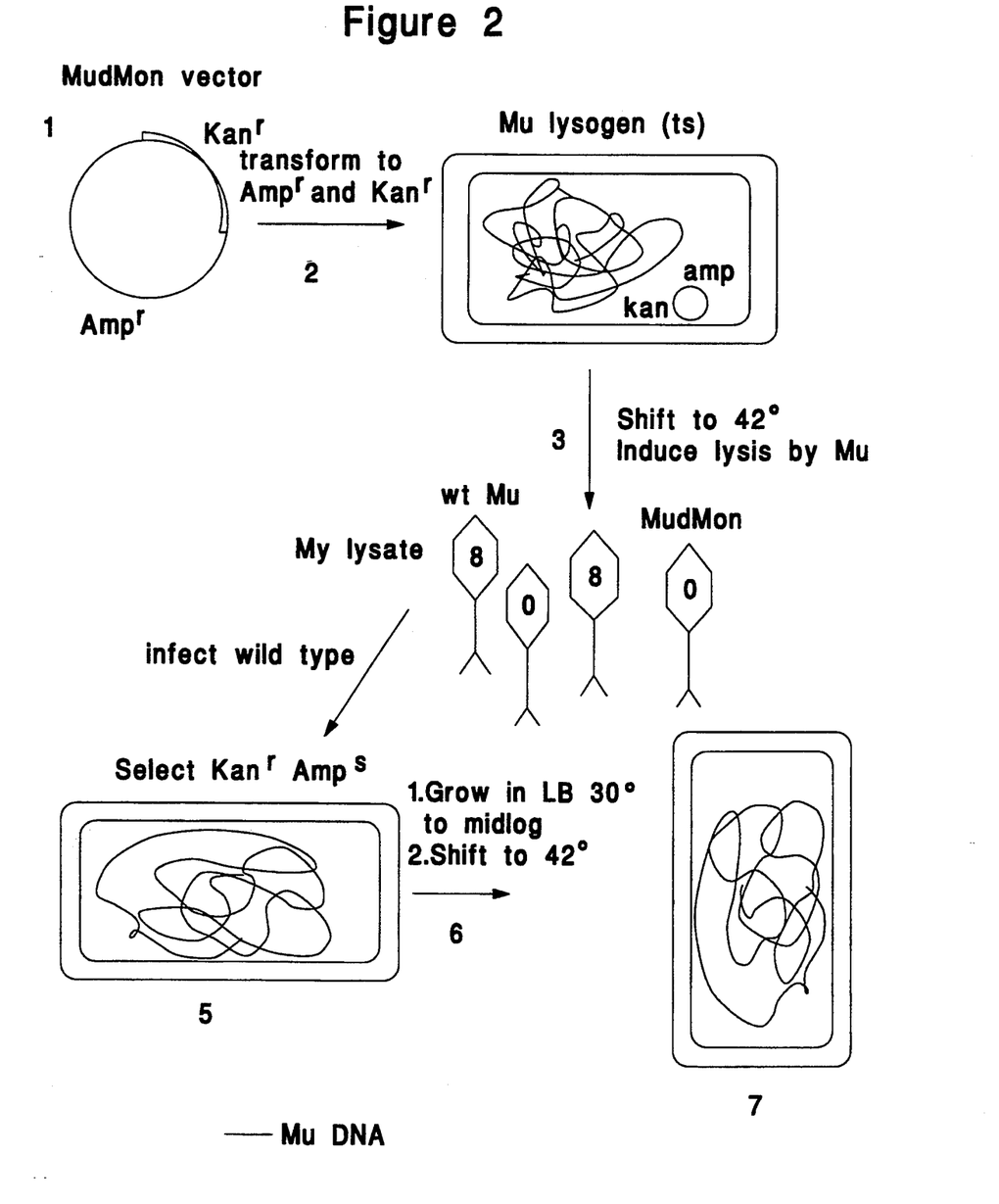

The ribosome binding site and translation enhancer region of bacteriophage T7 gene 10L (Olins and Rangwala, 1990) along with a multiple cloning site were cloned by PCR from pMON5766 as a BglII-BamHI fragment. This fragment was inserted downstream of Pm to increase translation initiation of the heterologous protein. This cloning resulted in the construction of MudMON200 (FIG. 1). The unique sites in the multiple cloning site were EcoRI, BamHI, ClaI and the XbaI site in g10L.

b. Construction scheme of mini-Mu lysogens for expression (FIG. 2 ).

Step 1. The gene of interest is cloned into the multiple cloning site of MudMON200 in the appropriate orientation by standard techniques.

Step 2. This plasmid is then introduced into a temperature-sensitive Mu lysogen such as MC1040 by transformation selecting for kanamycin-resistant, ampicillin-resistant colonies.

Step 3. To obtain a Mu lysate containing the Mu vector the transformants produced in step 2 are used to produce a lysate as described in Materials and Methods. This Mu lysate consists of phage particles that contain wild type Mu or the MudMON vector.

Step 4. To make the MudMON lysogen, a non-Mu lysogen such as MH4997 is transduced with Mu lysate produced in Step 3 as described previously.

Step 5. A fraction of the transduction mix, 0.1 ml, is then plated on LB agar containing kanamycin. The plate is incubated 1–2 days at 30° C. The kanamycin-resistant colonies are screened for ampicillin-sensitivity to ensure that the entire plasmid was not transferred.

Step 6. High level expression of the inserted gene is achieved by growing the MudMON lysogen in LB at 30° C. to mid-log phase. As was done in making the lysate an equal volume of pre-warmed LB is added and the culture is shifted to 42° C.

Step 7. Following temperature shift, the MudMON DNA undergoes replicative transposition and transcription occurs from the Mu middle promoter. By 4 h following temperature shift the cells can be harvested and the heterologous protein purified.

The broad host range of bacteriophage Mu should allow use of the MudMON vectors in a number of bacterial host strains such as Serratia, Erwinia, and Citrobacter. Other strains such as Pseudomonas and Agrobacterium are not sensitive to infection by Mu but are permissive for transposition of MuDNA (Castilho, et al. 1984). In these bacteria, the MudMON vector may be introduced on a suicide plasmid.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The following examples are provided to illustrate the present invention and are not intended to limit the scope thereof. Those skilled in the art will readily understand that known variations of the conditions and processes of the following preparative procedures can be used to prepare these cell lines.

Example 1. Expression of chloramphenicol acetyl transferase (CAT) from MudMON vector.

a. Construction and stability studies of MudMON vector encoding CAT.

As a first step to test whether the system would work, the cat gene was cloned into the BamHI site of MudMON100 from pCM4 resulting in MudMON101. The promoterless gene contained its cognate ribosome binding site. All the original cloning was done in the Mu lysogen MH3870 because it was reported that the mini-Mu plasmids were more stable in a Mu lysogen (Castilho, et al., 1984). The resident Mu in this strain is incapable of phage production due to an amber mutation in C, the inducer of late transcription. To construct a MudMON lysogen, the plasmid containing MudMON101 was transformed into MC1040 which is lysogenic for Mucts62. A Mu lysate made from this strain was used to transduce MH4997 selecting for $Km^r$ transductants and then scoring for $Ap^s$. Plasmid mini-preps were done to determine that no plasmid was present.

Figure 3:
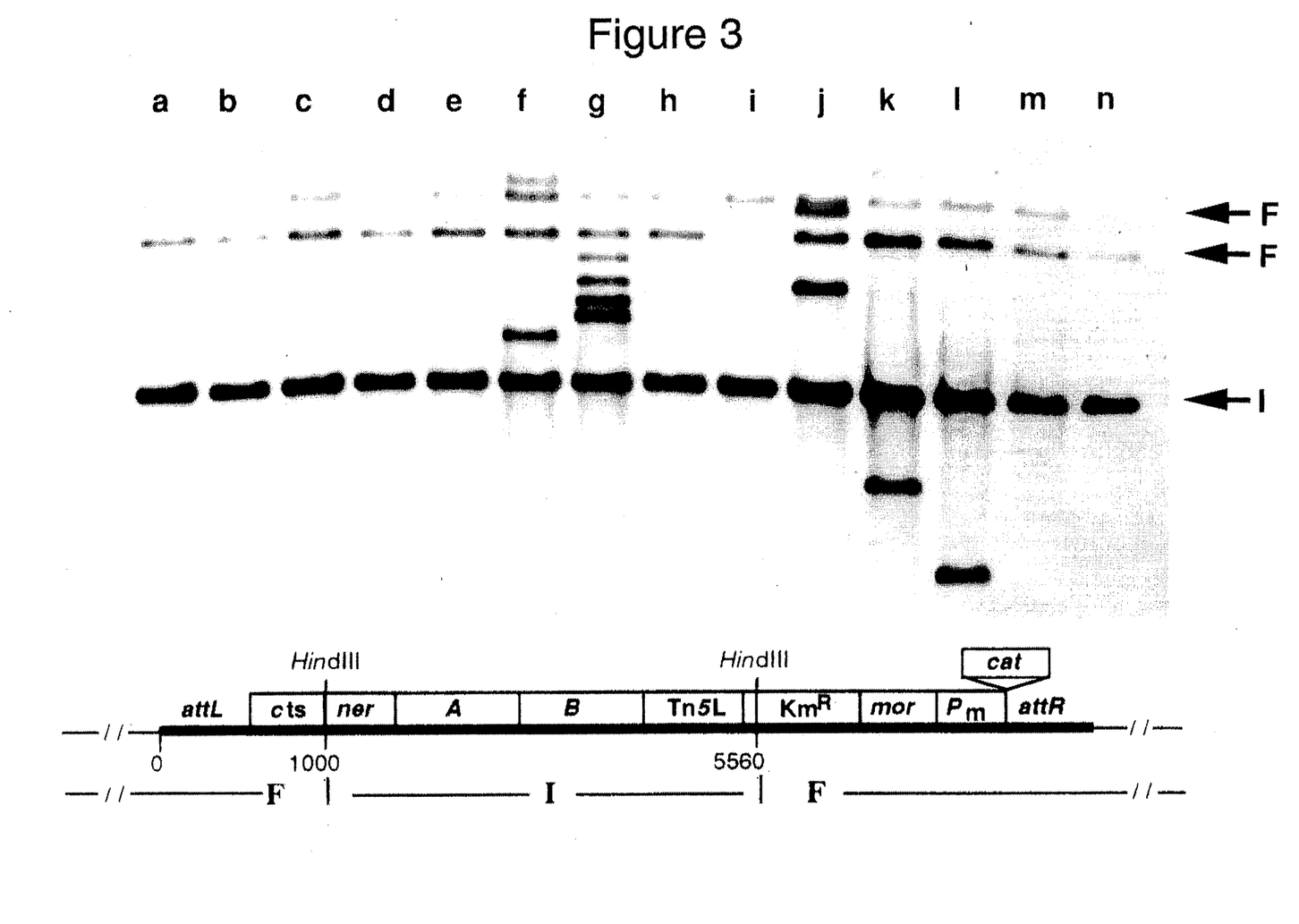

One advantage that is gained from a chromosomal based expression system is increased stability of the vector in the absence of selective pressure. To test this prediction, three MH4997(MudMON101) isolates were grown non-selectively in LB for 7 d. Each day a $10^6$ dilution was made in fresh LB. After 7 d, cells were plated for single colonies on LB $\mp$Km. Equal numbers of colonies appeared on both types of plates, suggesting that the MudMON101 insertion was very stable. To test more rigorously that the vector was stable, six colonies were picked from one of the Km plates and 6 from the corresponding plate lacking antibiotic. The colonies were grown up overnight and DNA was isolated. Southern blot analysis was done to determine if any gross rearrangement had occurred (FIG. 3). In all but one instance (lane i) the original pattern was retained. However, there were a number of cases where a second insert was evident (lanes f, j, k and l) and one where a third insertion could be detected (lane g). None of these secondary inserts was the same suggesting that the transposition occurred very late in the subculturing.

b. Inductions

Figure 4A:
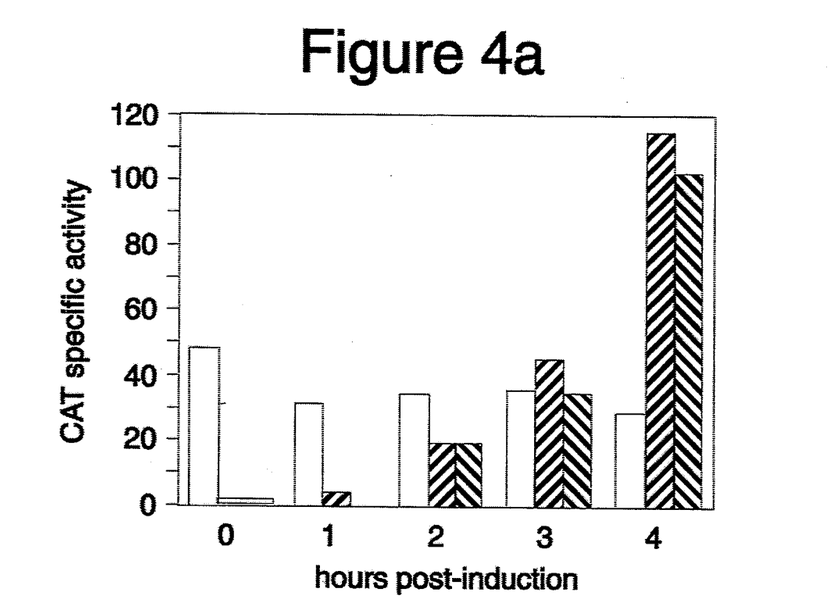
Figure 4B:
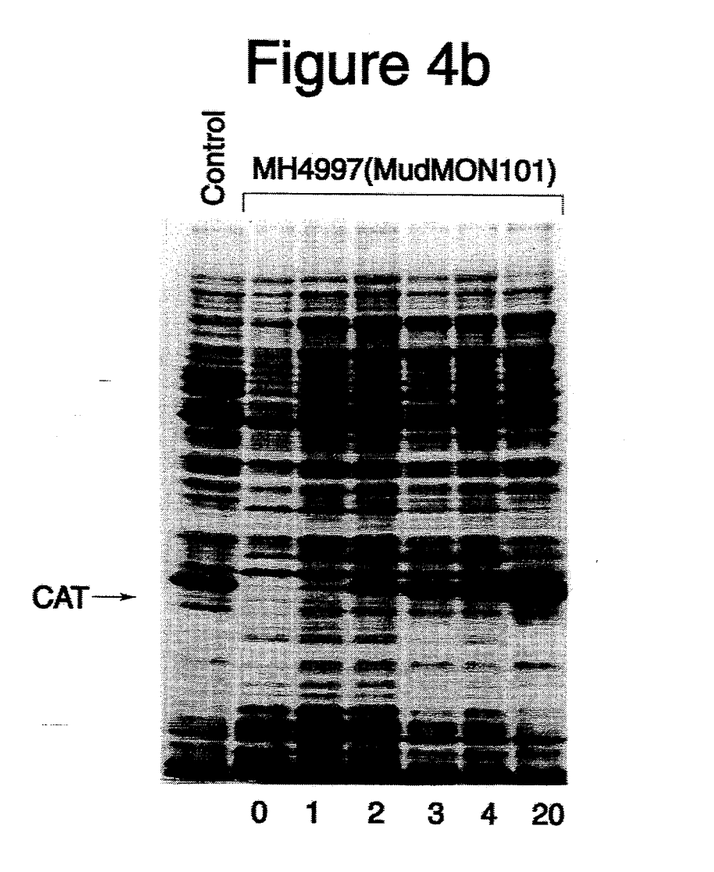

A number of MudMON101 lysogens were induced by temperature shift as described above and the cultures assayed for chloramphenicol acetyl transferase (CAT) activity at various time points post-induction. The degree of induction of cat expression increased 30 to 40 fold by 4 h post-induction (FIG. 4A). The level of CAT at 4 h exceeded that observed in JM101[pACYC184] where CAT was expressed constitutively from its own promoter. The level of CAT accumulation was also monitored by SDS-PAGE (FIG. 4B).

Figure 4C:
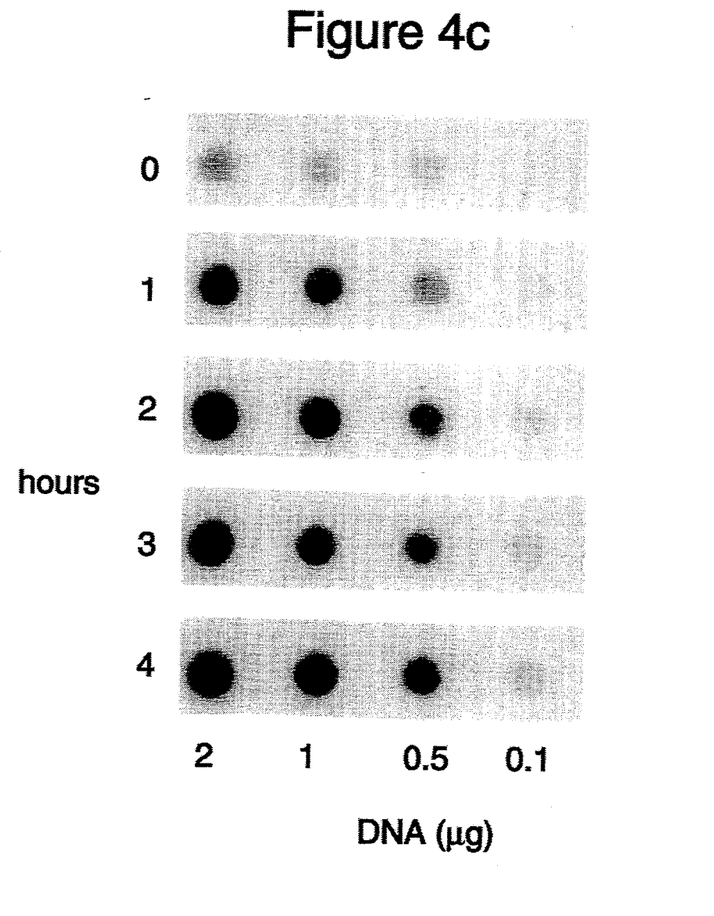

Dot blots were done to correlate the increase in expression with increase in copy number of MudMON101 (FIG. 4C). An increase in the copy number of MudMON101 was seen as early as 1 h post-induction while an increase in CAT activity was not seen until 2-3 h post-induction. The reason for the delay in expression relative to replication was not clear.

c. Transcriptional Regulation of Cloned Gene

The MudMON vectors were constructed in such a way that expression from Pm was dependent on expression of mor from the nptII promoter (PnptII). It seemed possible that the expression of the heterologous gene observed was not due to transcription from Pm but rather from PnptII. To test this possibility, the cat gene with its ribosome binding site was cloned into the BamHI site of pBC4041, placing the gene downstream of nptII, at the same site as mor in MudMON100. Lysogens were made and inductions were done as described in FIG. 2. There appeared to be little to no synthesis of CAT (data not shown). These results suggested that expression in the MudMON vectors was indeed due to transcription from Pm.

As a further test to determine if mor was required for expression, nptII including its promoter was deleted as an XhoI fragment from the MudMON101 containing plasmid. This deletion retained IS50L from Tn5 which should result in a polar effect (Berg, 1989) and prevent read-through transcription from Pe. Since this construct left no selection for lysogens, inductions were done on plasmid-containing cells. A control was run with the nptII containing plasmid. The control induction resulted in levels of CAT comparable to that obtained with the lysogen. The constructs without the nptII gene expressed very little CAT (data not shown). These results suggested that Mor was being produced from read-through transcription from PnptII and was necessary for expression of CAT from Pm.

d. Strain Variation

Figure 5:
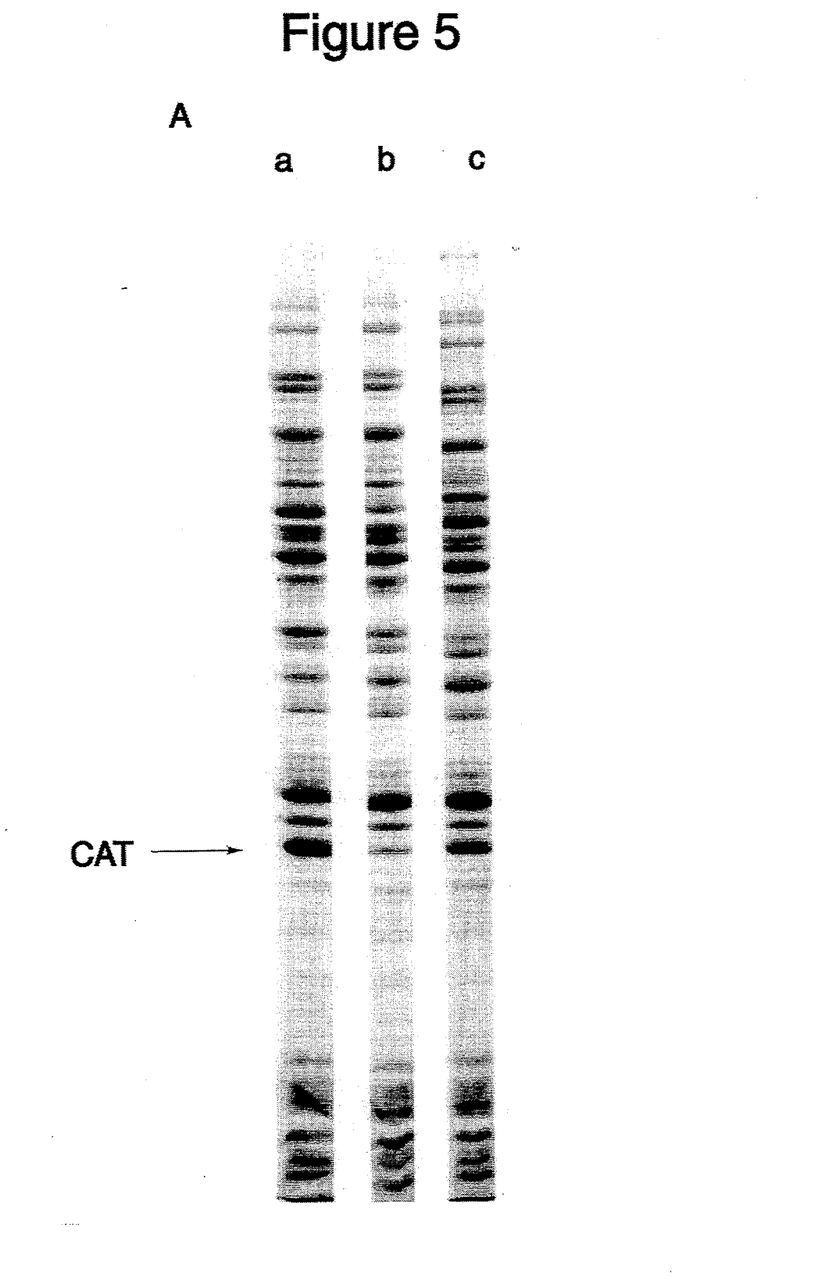
FIG. 5. Induction of MudMON101 lysogens in different strains. Lysogens of MudMON101 were made in MH4997(a), W3110G (b) and JM101(c). Inductions were done and accumulation of CAT was analyzed by SDS-PAGE 4 h post-induction.

All MudMON induction experiments described to this point were done in MH4997. Since expression of heterologous genes has been shown to vary in different strains, lysogens containing MudMON101 were made in a number of different strains; JM101, W3110G and MH2374. W3110G was selected because this is the strain routinely used for expression of pST in the laboratory. The highest level of expression was seen in MH4997 and little to no expression was observed in W3110G (FIG. 5). The level of expression in JM101 was moderate for CAT. The reason for these strain differences was not obvious from the genotype of the strains.

Dot blots were done to determine if strain variation could be explained by the difference in the ability of MudMON to replicate. DNA was isolated before and 4 h post-induction from MudMON101 lysogens of JM101, W3110G, and MH4997. The DNA was probed with the nptII gene to determine copy number. In each case, the copy number was approximately 50. These results suggested that copy number was not the sole determinant of expression level. (Data not shown).

e. Media Studies

Figure 6:
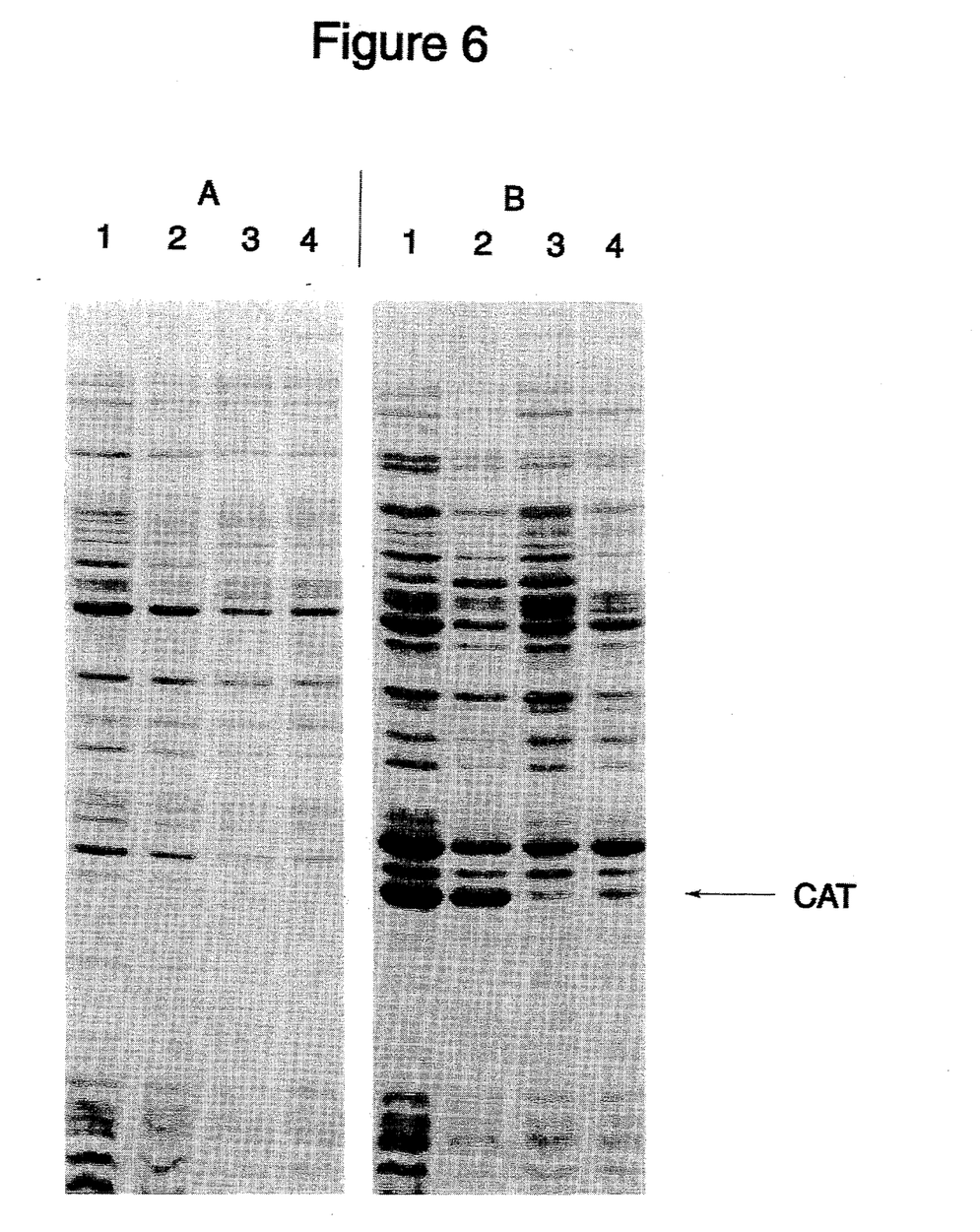
FIG. 6. Effect of media on expression levels of CAT from MudMON101. MH4997(MudMON101) was grown in four different media for inductions, SB(1), LB(2), 2X M9 minimal(media)(3) and M9 minimal media(4). Accumulation level of CAT was measured by SDS-PAGE. The samples prior to temperature shift are in panel A and those in panel B are 6 h post-induction.

All the inductions described were done in LB since, in general, phage replicate best in rich media. However, expression of heterologous genes is often done in defined media since it is cheaper and more reproducible. Inductions were done growing MH4997(MudMON101) in M9+1% CAA, 2X M9+2% CAA, LB and SB (FIG. 6). Maximum expression was found with SB followed by LB. Very little to no CAT was produced in the defined media. Dot blots were done to determine if the low level of expression was due to an inability of the mini-Mu to replicate in the defined media (data not shown). The number of copies of MudMON101 4 h post-induction appeared to be approximately 60–70 for cells grown in LB, SB and 1X M9-CAA. The number of copies present in the culture grown in 2X M9-CAA appeared to be about 4 fold lower. Although in one instance both copy number and expression were low (2X M9-CAA), in the case of 1X M9-CAA the low level of expression did not correlate with a lower copy number. These data suggested that other factors must be affecting expression.

Example 2. Expression of β-galactosidase from MudMON vector a. Inductions

Figure 7:
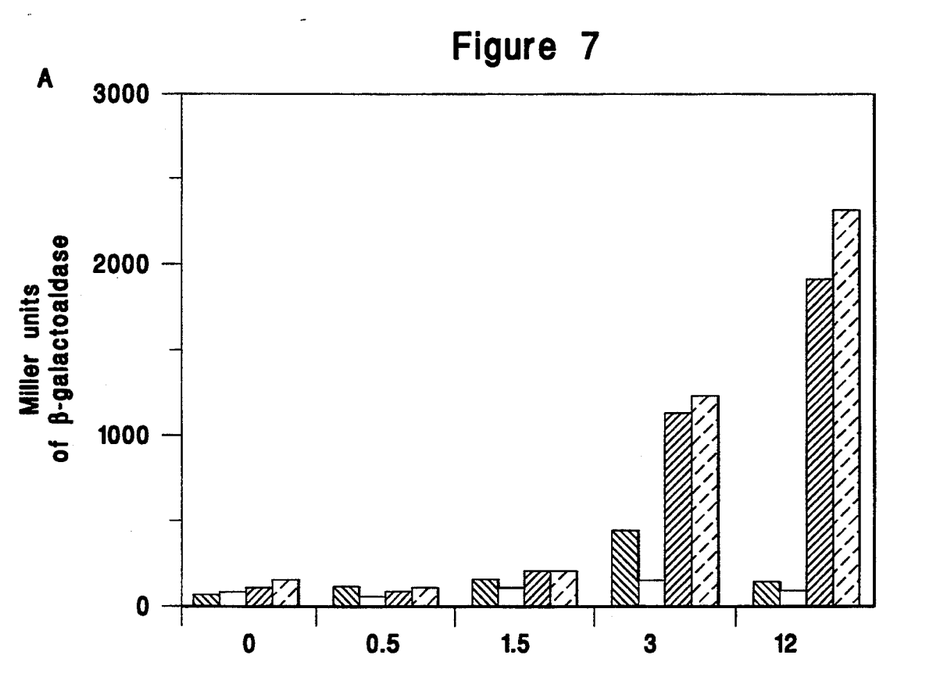

The lacZ gene was cloned into the BamHI site of MudMON101 as a BamHI-BglII fragment from pLRKD211 resulting in MudMON102. As was the case with Cat, the lacZ gene contained its cognate ribosome binding site. Again as with cat, all the original cloning was done in the Mu lysogen MH3870 and transformed into MC1040 for preparation of the Mu lysate. MudMON102 was then transduced into MH4997. A number of MudMON102 lysogens were induced by temperature shift as described above and the cultures assayed for β-galactosidase (βGal) activity at various time points post-induction. The level of βGal activity was 10–20 fold higher 3 h post-induction compared to the pre-induction level (FIG. 7).

b. Transcriptional Regulation of Cloned Gene

Studies were also done with lacZ to ensure that expression was dependent on $P_m$ as was the case for cat. lacZ with its cognate ribosome binding site was cloned into the BamHI site of pBC4041, placing the gene downstream of nptII, at the same site as mor in MudMON100. Lysogens were made and inductions were done as previously described. There appeared to be little to no synthesis of β-Gal (data not shown). These results suggested that expression of lacZ from MudMON102 was indeed due to transcription from Pm as had been shown for MudMON101.

Figure 8A:
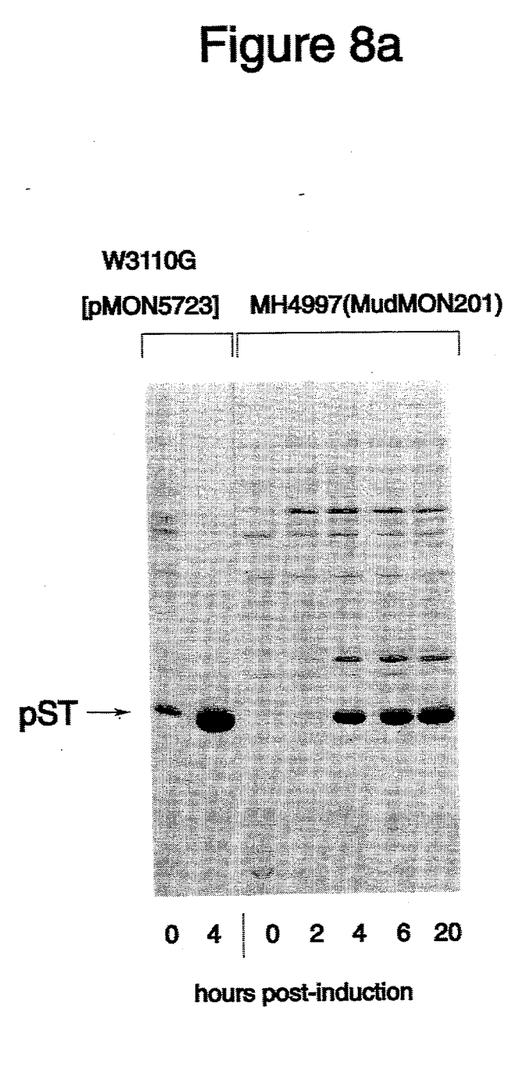
FIG. 8a and 8b. Production of pST from MudMON201 lysogens.

Example 3. Expression of porcine somatotropin (pST) from MudMON vector a. Inductions The heterologous gene porcine somatotropin, pST, (Seeburg, et al., 1983) was cloned into MudMON200 as an XbaI fragment from pMON5723 resulting in MudMON201. Lysogens were made in MH4997. Inductions were done as described above. By 4 h post-induction pST accounted for approximately 20% of total cell protein. The level of pST which accumulated was approximately ¼ of that seen when the protein was synthesized from a standard plasmid expression vector, pMON5723 (FIG. 8a).

b. Transcriptional Regulation of Cloned Gene

One approach that was used with cat to determine if expression was dependent on mor and $P_m$ was also tried with pST. The nptII gene including its promoter was deleted as an XhoI fragment from the MudMON201 containing plasmid. This deletion retained IS50L from Tn5 which should result in a polar effect (Berg, 1989) and prevent read-through transcription from Pe. Since this construct left no selection for lysogens, inductions were done on plasmid-containing cells. A control was run with the nptII containing plasmid. The control inductions resulted in levels of pST comparable to that obtained with the lysogen. The constructs without the nptII gene expressed very little pST (data not shown). These results suggested that Mor was being produced from read-through from the nptII promoter and was necessary for expression from Pm. The same results were obtained with CAT.

c. Strain Variation

Figure 8B:
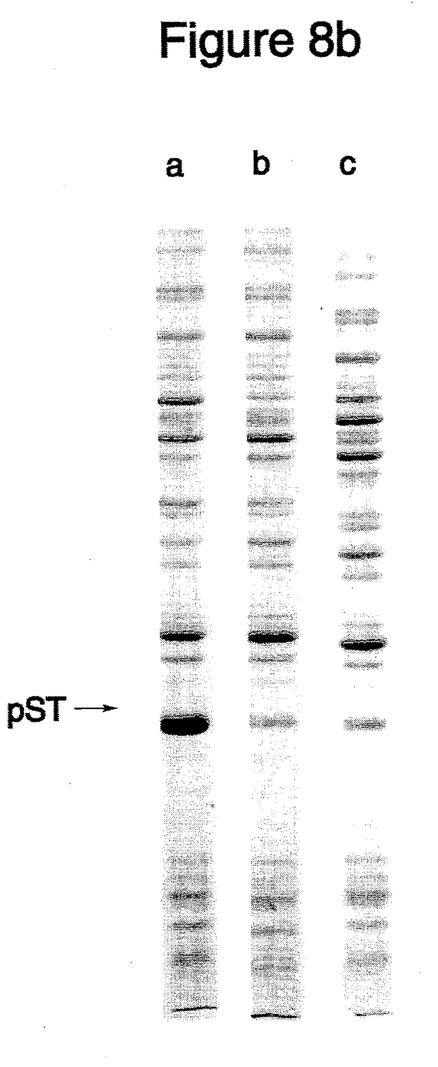

MudMON201 lysogens were made in the same strains as were tried for MudMON101; MH4997, JM101, W3110G and MH2374. For pST as was true for CAT, the highest level of expression was seen in MH4997 and little to no expression was observed in W3110G (FIG. 8b). The level of expression in JM101 was protein dependent; it was moderate for CAT and low for pST.

As was the case with cat, dot blots results suggested that copy number was not the sole determinant of expression level. (Data not shown).

It seemed possible that the lack of expression of the heterologous gene in some strains could be due to insufficient amounts of Mor being synthesized due to differences in transcriptional read-through. To test this hypothesis, Mor was expressed in trans from pKM78 which contains the mor gene under the control of the lacUV5 promoter, in MudMON201 lysogens of MH4997, JM101 and W3110G. Inductions were done using temperature shift alone, temperature shift plus IPTG, or IPTG alone. Expression of pST in all strains was not enhanced by expressing mor in trans (data not shown).

A further test of the level of Mor in the cells was performed by introducing pKM32 which has lacZ under the control of $P_m$, into MudMON201 lysogens of MH4997, W3110G and MH2374. As controls, pKM32 was present in the Mu lysogen MH3870 as well as a non-Mu lysogen containing pKM78. All the MudMON lysogens expressed βGal at very high levels. All were above those seen with the Mu lysogen MH3870. These two sets of experiments suggested that Mor was not limiting in any of the MudMON lysogens. The results also suggested that the Mor made was capable of inducing Pm.

Figure 9A:
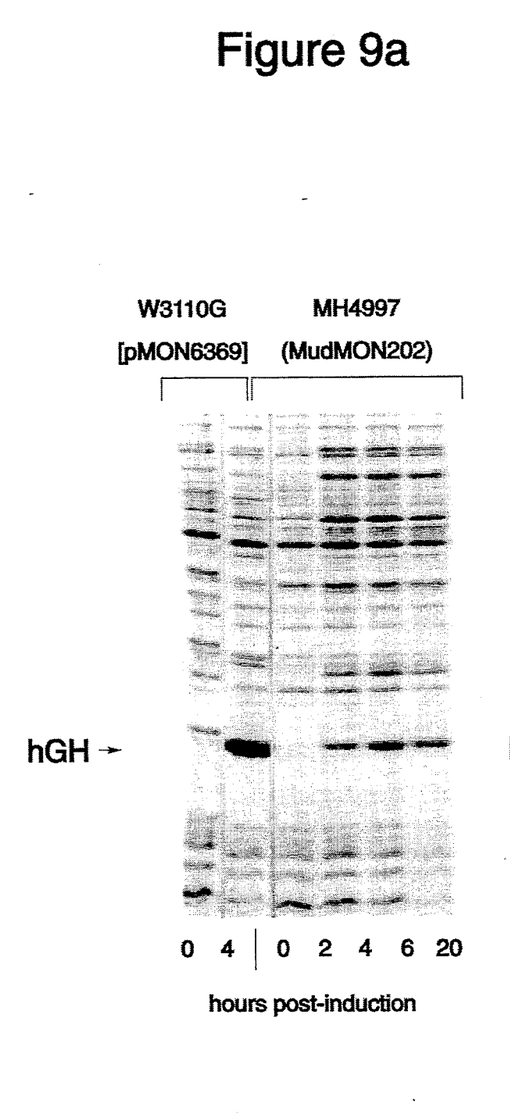
FIG. 9a and 9b. Accumulation of hGH from Mud-MON202 lysogens.

Example 4. Expression of human growth hormone (hGH) from MudMON vector a. Inductions The heterologous gene for human growth hormone (hGH) was inserted into MudMON200 as an XbaI fragment from pMON6369 resulting in MudMON202. Lysogens were made in MH4997. Inductions were performed in LB. By 4 h post-induction the level of hGH was approximately 5% of total cell protein (FIG. 9). The relative level of hGH from MudMON202 compared to the plasmid vector was not as high.

b. Strain Variation

Figure 9B:
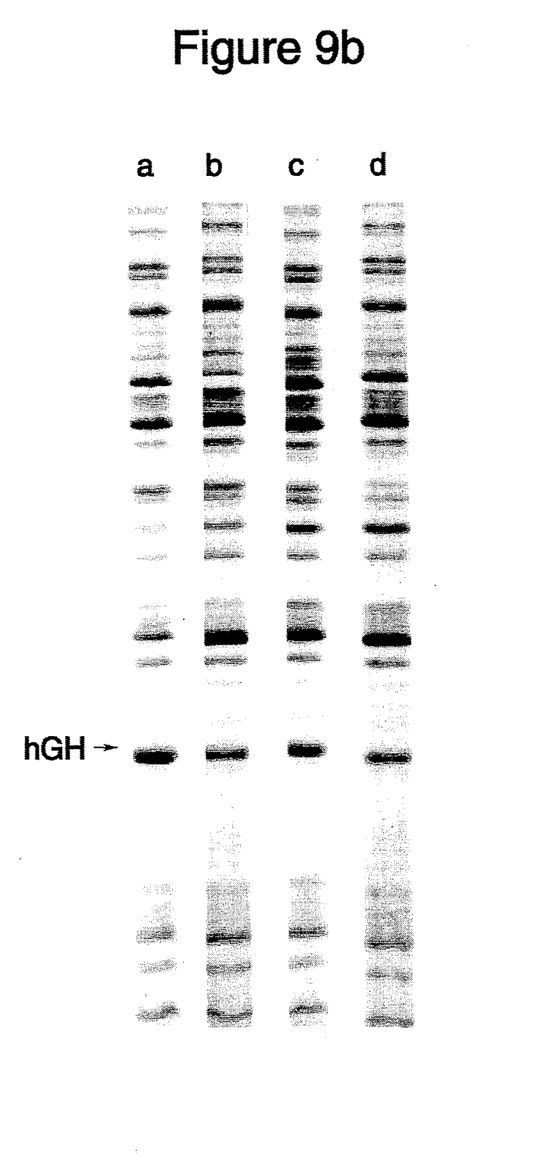

Lysogens containing MudMON202 were made in the same set of strains that had been used with MudMON101 and MudMON201; JM101, W3110G and MH2374. MH2374 was chosen since it is an excellent host for Mu. Contrary to the results seen with CAT and pST, the level of hGH was equivalent in all four strains (FIG. 9b). Again the copy number was the same for all strains (data not shown).

The experiments described to determine the level of Mor in MudMON201 lysogens were done with the MudMON202 lysogens yielding similar results, in all cases the level of Mor did not appear to be limiting (data not shown).

TABLE 1

| Strain list | | |
|---|---|---|
| Strain | Features | Source |
| JM101 | F' traD36 proA+ proB+ lacIq lacZΔM15/supE thi D(lac-proAB) | Lab collection |
| MC1040 | (F - araD139 ara::(Mucts)3 | M. |

TABLE 1-continued

Strain list

| Strain | Features | Source |
|---|---|---|
| MH2374 | Δ(lac)x74 galU galK rpsL araD thi | Casadaban M. Howe |
| MH3870 | thyA malT::(Mu cts62 Cam4005) | M. Howe |
| MH4997 | W3110 thyA | M. Howe |
| W3110G | tonA | Genentech |
| Phage | | |
| Mud4041 | $Km^r$ | Castilho, et al., 1984 |
| MudMON100 | Mud4041 + mor and $P_m$ | FIG. 1 |
| MudMON101 | MudMON100 + cat (BamHI fragment of pCM4) | This work |
| MudMON102 | MudMON100 + lacZ (BglII-BamHI fragment of pLRKΔ211) | This work |
| MudMON200 | MudMON100 + g10L and MCS | FIG. 1 |
| MudMON201 | MudMON200 + pST (XbaI fragment of pMON5723) | This work |
| MudMON202 | MudMON200 + hGH (XbaI fragment of pM ON6369) | This work |
| Plasmids | | |
| pBC4041 | pUC::Mud4041, $Ap^r$, $Km^r$ | Castilho, et al., 1984 |
| pCM4 | cat cartridge (BamHI) | Pharmacia |
| pKM32 | pBR322 derivative; $P_m$ lacZ, $Ap^r$ | Mathee and Howe, 1990 |
| pKM78 | pACYC derivative; $P_{lacUV5}$e16e17, $Cm^r$ | Mathee and Howe, 1990 |
| pLRKΔ211 | Tn5 lac | Kroos and Kaiser, 1984 |
| pMON5723 | pMON5766 + pST | Lab collection |
| pMON5766 | pBR327 derivative, φT7 g10L, MCS, $Ap^r$ | Olins and Rangwala, 1990 |
| pMON6369 | pMON5766 + hGH | Lab collection |
| pWM6 | pBR322 derivative, Mu DNA from 5.1–10.7 kbp | Margolin and Howe, 1986 |

REFERENCES

Ausubel, F. M., R. Brent, R. E. Kingston, D. D. Moore, J. G. Seidman, J. A. Smith and K. Struhl ed.: Current Protocols in Molecular Biology, John Wiley and Sons. New York, 1989.

Berg, D. E.: Transposon Tn5, in Howe, M. M. and Berg, D. E. (Eds.) Mobile DNA. American Society for Microbiology, Washington, D.C., 1989, pp. 185–209.

Castilho, B. A., Olfson, R. and Casadaban, M. J.: Plasmid insertion mutagenesis and lac gene fusion with mini-Mu bacteriophage transposons. J. Bacteriol. 158 (1984) 488–495.

Gerdes, K.: The parB (hok/sok) locus of plasmid R1: A general purpose plasmid stabilization system. Bio/technology 6 (1988) 1402–1405.

Kroos, L. and Kaiser, D.: Construction of Tn5 lac, a transposon that fuses lacZ expression to exogenous promoters, and its introduction into Myxococcus xanthus. Proc. Natl. Acad. Sci. USA 81 (1984) 5816–5820.

Laemmli, U. K.: Cleavage of structural proteins during the assembly of the head of bacteriophage T4. Nature 227 (1970) 680–685.

Margolin, W. and Howe, M. M.: Localization and DNA sequence analysis of the C gene of bacteriophage Mu, the positive regulator of Mu late transcription. Nucl. Acids Res. 14 (1986) 4881–4897.

Margolin, W., Rao, G. and Howe, M. M.: Bacteriophage Mu late promoters: four late transcripts initiate near a conserved sequence. J. Bacteriol. 171 (1989) 2003–2018.

Marrs, C. F. and Howe, M. M.: Kinetics and regulation of transcription of bacteriophage Mu. Virology 174 (1990) 192–203.

Mathee, K. and Howe, M. M.: Identification of a positive regulator of the Mu middle operon. J. Bacteriol. 172 (1990) 6641–6650.

Miller, J. H.: Experiments in Molecular Genetics. Cold Spring Harbor Laboratory, Cold Spring Harbor, N.Y., 1972.

Nakano, E. and Masuda, T.: Construction of sleeper cloning vehicles for enzyme overproduction. Agric. Biol. Chem. 46 (1982) 313–315.

Obukowicz, M. G., Turner, M. A., Wong, E. Y. and W. C. Tacon, W. C.: Secretion and export of IGF-1 in Escherichia coli strain JM101. Mol. Gen. Genet. 215 (1988) 19–25.

Olins, P. O. and Rangwala, S. H.: Vector for enhanced translation of foreign genes in Escherichia coli. Methods Enzymol. 185 (1990) 115–119.

Padukone, N., Peretti, S. W. and Ollis, D. F.: 1 vectors for stable cloned gene expression. Biotechnol. Prog. 6 (1990) 277–282.

Panasenko, S. M., Cameron, J. R., Davis, R. W. and Lehman, I. R.: Five hundredfold overproduction of DNA ligase after induction of a hybrid lambda lysogen constructed in vitro. Science 196 (1977) 188–189.

Pato, M. L. and Waggoner, B. T.: Replication of Mu DNA in vivo, in Symonds, N., Toussaint, A., Van de Putte, P. and Howe, M. M(Eds.), Phage Mu. Cold Spring Harbor Laboratory, Cold Spring Harbor, N.Y., 1987, pp.177–189.

Porter, R. D., Black, S., Pannuri, S., and Carlson, A.: Use of the Escherichia coli ssb gene to prevent bioreactor takeover by plasmidless cells. Bio/technology 8 (1990) 47–51.

Priess, H., Schmidt, C. and Kamp, D.: Mu DNA sequences, part A: Sequence of the left end of Mu. in Symonds, N., Toussaint, A., Van de Putte, P. and Howe, M. M (Eds.), Phage Mu. Cold Spring Harbor Laboratory, Cold Spring Harbor, N.Y., 1987, pp. 277–296.

Seeburg, P. H., Stacey, S., Adelman, J., deBoer, H. A., Hayflick, J., Jhurani, P., Goeddel, D. V. and Heynekeer, H. L.: Efficient bacterial expression of bovine and porcine growth hormones. DNA 2 (1983) 37–45.

Shaw, W. V.: Chloramphenicol acetyltransferases from chloramphenicol-resistant bacteria. Methods Enzymol. 43 (1975) 737–755.

Skogman, G., Nilsson, J. and Gustafsson, P.: The use of a partition locus to increase stability of tryptophan-operon-bearing plasmids in Escherichia coli. Gene 23 (1983) 105–115.

Stoddard, S. F. and Howe, M. M.: Localization and regulation of bacteriophage Mu promoters. J. Bacteriol. 171 (1989) 3440–3448.

Stoddard, S. F. and Howe, M. M.: Characterization of the C operon transcript of bacteriophage Mu. J. Bacteriol. 172 (1990) 361–371.

Summers, D. K.: The kinetics of plasmid loss. Tibtech. 9 (1991) 273–278.

Summers, D. K. and Sherratt, D. J.: Multimerization of high copy number plasmids causes instability: ColE1 encodes a determinant essential for plasmid monomerization and stability. Cell 36 (1984) 1097–1103.

Zund, P. and Lebek, G.: Generation time-prolonging R plasmids: correlation between increases in the generation time of Escherichia coli caused by R plasmids and their molecular size. Plasmid 3 (1980) 65–69.

From the foregoing description, one skilled in the art can easily ascertain the essential characteristics of this invention, and without departing from the spirit and scope thereof, can make various changes and modifications of the invention to adapt it to various usages and conditions. Accordingly the scope of the invention is not to be considered limited to the particular embodiments shown of suggested, but is rather to be determined by reference to the appended claims.

What is claimed is:

1. A Mini Mu Vector, comprising:

Mu elements required for replicative transposition which consist essentially of the Mu A and B transposition genes, the two attachment sites attL and attR, and the genes encoding the regulatory proteins cts62 and ner all of which are in the order shown in FIG. 1; and a Mu mor gene, a mu middle promoter, a ribosome binding site linked to at least one unique restriction site, and a gene encoding a selectable marker all of which are operably linked and in proper reading frame to a DNA insert comprising codons for a heterologous polypeptide.

2. The Mini Mu Vector as recited in claim 1 wherein said DNA insert encodes for chloramphenicol acetyl transferase, β-galactosidase, porcine somatotropin or human growth hormone.

3. A bacterium transformed by the Mini Mu vector of claim 1 which is selected from the group consisting of Serratia, Erwinia, Citrobacter, and *E. coli*.

4. The bacterium as recited in claim 3 wherein said bacterium is *E. coli*.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

ATGCCAGAAA GATCTGGAGG ATG        23

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

TTCCCCGGAT CCGTTATTCA        20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

GGCGCGTGGA TCCGCTATCG        20

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

ACAGAACAGA TCTGGGCCCT TC        22